United States Patent [19]

Lutomski et al.

[11] Patent Number: 4,791,124
[45] Date of Patent: Dec. 13, 1988

[54] PHOTOACTIVE AZOLE PESTICIDES

[75] Inventors: Kathryn A. Lutomski, Hightstown; Susan E. Burkart, Trenton, both of N.J.; Richard B. Phillips, Diamond Bar, Calif.; David M. Roush, Princeton, N.J.; Ignatius J. Turchi, Yardley, Pa.

[73] Assignee: FMC Corporation, Philadelphia, Pa.

[21] Appl. No.: 34,259

[22] Filed: Apr. 2, 1987

Related U.S. Application Data

[63] Continuation-in-part of Ser. No. 857,883, Apr. 30, 1986, abandoned, and a continuation-in-part of Ser. No. 908,754, Sep. 17, 1986, abandoned.

[51] Int. Cl.$^4$ .................. A01N 43/76; A01N 43/78; C07D 413/02; C07D 417.14
[52] U.S. Cl. ........................... 514/365; 514/63; 514/374; 548/110; 548/203; 548/204; 548/205; 548/235; 548/236
[58] Field of Search ............... 548/110, 202, 235, 203, 548/204, 209, 236; 514/63, 365, 374

[56] References Cited

U.S. PATENT DOCUMENTS 4,153,703  5/1979  Harrison et al. .................. 424/270

OTHER PUBLICATIONS

Hayes et al, Chemical Abstracts, vol. 51 (1957) 16126e.
Kerr et al, Chemical Abstracts, vol. 54 (1960) 9891c.
Chauvin et al, Chemical Abstracts, vol. 82 (1979) 125314d.
T. Sakamoto, et al., "Palladium-Catalyzed Reactions of Terminal Acetylenes and Olefins with Halo-1,3-azoles", Chem. Pharm. Bull., 35(2), 823–828, (1987).
Hayes . . . et al. "Pulse Height Comparison of Primary Solutes", Nucleonics 13, No. 12, 38–41 (1955).
Kerr . . . et al. "Liquid Scintillators, VIII. The Effect of the Dialkylamino Group", J. Org. Chem. 24, 1864–66 (1959).
Chauvin et al., Bull. Soc. Chem. de France, No. 9–10, 2099–2104 (1974).

Primary Examiner—Richard L. Raymond
Attorney, Agent, or Firm—Robert L. Andersen; H. Robinson Ertelt

[57] ABSTRACT

Oxazole and thiazole compounds of the following formula are photodynamic insecticides and acaricides as well as nematicides:

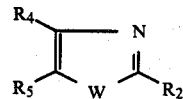

wherein
W is selected from O and S;
$R_2$ is selected from optionally substituted thienyl and optionally substituted phenyl;
$R_4$ is selected from hydrogen, lower alkyl, lower haloalkyl, thienyl, tri(lower alkyl)silyl, and optionally substituted phenyl;
$R_5$ is selected from optionally substituted thienyl and optionally substituted phenyl;
at least one of $R_2$ and $R_5$ is an optionally substituted thienyl group, and $R^4$ is other than hydrogen when $R^4$ and $R^5$ are each unsubstituted phenyl or thienyl.

10 Claims, No Drawings

PHOTOACTIVE AZOLE PESTICIDES

This application is a continuation-in-part of application Ser. No. 857,883, filed Apr. 30, 1986, now abandoned, and Ser. No. 908,754, filed Sept. 17, 1986, now abandoned.

This invention is in the field of heterocyclic organic chemical compounds which contain an azole nucleus. More particularly, the invention includes certain oxazole and thiazole compounds per se, agricultural compositions containing the novel compounds, and the method of using a broad class of such compounds to control agricultural pests such as insects, acarids and nematodes.

There is increasing scientific evidence that toxic mechanisms initiated by light play an important role in natural control of certain pest populations. In the last few years the concept of using photoactive agents as insecticides has been advanced. Such photosensitizers typically display insecticidal activity by catalyzing the electronic triplet to singlet conversion of molecular oxygen. The excited singlet oxygen behaves as a super oxidizing agent, destroying the insect tissues which it contacts, hence killing the insect.

According to the present invention, oxazole/thiazole compounds of the following structural formula are photodynamic insecticides and acaricides, as well as nematicides:

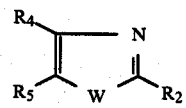

wherein

W is selected from O and S;

$R_2$ is selected from optionally substituted thienyl and optionally substituted phenyl;

$R_4$ is selected from hydrogen, halogen, lower alkyl, lower haloalkyl, thienyl, tri(lower alkyl)silyl, and optionally substituted phenyl;

$R_5$ is selected from hydrogen, lower alkyl, optionally substituted thienyl, or optionally substituted phenyl; provided, however, that at least one of $R_2$ and $R_5$ is an optionally substituted thienyl group, and $R_4$ is other than hydrogen when one of $R_2$ and $R_5$ is unsubstituted thienyl and the other of $R_2$ and $R_5$ is unsubstituted phenyl.

Substituents which optionally may be carried by phenyl include one or more of the following, independently selected: hydrogen, halogen, lower alkyl, lower haloalkyl, lower alkoxy, lower haloalkoxy, cyano, dialkylamino, phenyl, pyridyl, thienyl, lower alkylsulfonyloxy, thiobenzoyl, phenylsulfonyloxy, nitro, or —$C_4H_4$—, —$OC(X)_2O$—, —$OCF_2CF_2$—, or —$OC(CH_3)_2CH_2$—, —$OCX_2CX_2O$— bridging adjacent ring positions, wherein X is hydrogen, fluoro or methyl.

Thienyl optionally may carry a substituent independently selected from: hydrogen, halogen, lower alkyl, lower hydroxyalkyl, lower alkylthio, lower haloalkylthio, lower alkylsulfonyl, lower haloalkenylthio, thienyl, tri(lower)alkylsilyl, or lower alkoxycarbonyl.

More particularly the invention provides pesticidal compounds of the foregoing structural formula in which W is as defined above;

$R_2$ is selected from the group consisting of phenyl, naphthyl, 2,2-difluoro-1,3-benzodioxyl, phenyl substituted with at least one substituent selected from halogen, lower alkyl, lower haloalkyl, cyano, lower alkoxy, lower haloalkoxy, di(lower)alkylamino, phenylthiocarbonyl, or phenylsulfonyloxy, thienyl, and thienyl substituted with a substituent selected from halogen, lower alkyl, or thienyl;

$R_4$ is selected from the group consisting of hydrogen, tri(lower)alkylsilyl, phenyl, halophenyl, and thienyl;

$R_5$ is selected from the group consisting of hydrogen, lower alkyl, phenyl, phenyl substituted with at least one substituent selected from halogen, lower alkyl, lower haloalkyl, lower alkoxy, phenyl, or nitro, thienyl, and thienyl substituted with a substituent selected from lower alkyl, halogen, lower hydroxyalkyl, lower haloalkyl, lower alkylsulfonyl, lower haloalkenylthio, lower alkoxycarbonyl, or tri(lower)alkylsilyl. At least one of $R_2$ and $R_5$ is an optionally substituted thienyl group, preferably an optionally substituted 2-thienyl group, and $R_4$ is other than hydrogen when one of $R_2$ and $R_5$ is unsubstituted thienyl and the other of $R_2$ and $R_5$ is unsubstituted phenyl.

The terms "halo" or "halogen" when employed herein mean fluorine, chlorine or bromine. The term "lower" modifying "alkyl," "alkoxy," and the like means a straight or branched hydrocarbon chain of 1–6, preferably 1–4, carbon atoms; "halo," "hydroxy," etc. coupled with another term means one or more hydrogen atoms has been replaced by halogen or hydroxy, respectively.

Among the aforesaid compounds, the thiazoles are preferred, and, in the most active compounds, $R_4$ is hydrogen. Furthermore, it is preferred that $R_5$ be a 5-substituted thienyl substituent.

Specific preferred pesticides include the following compounds: 5-(5-methylthien-2-yl)-2-(4-trifluoromethylphenyl)thiazole, 5-(5-methylthien-2-yl)-2-[3,5-bis(-trifluoromethyl)phenyl]thiazole, 2-(4-fluorophenyl)-5-(thien-2-yl)thiazole, 2-(4-chlorophenyl)-5-(thien-2-yl)thiazole, 2-(4-trifluoromethylphenyl)-5-(thien-2-yl)thiazole, 5-(5-chlorothien-2-yl)-2-(4-fluorophenyl)thiazole, 2-(4-methylphenyl)-5-(5-methylthien-2-yl)thiazole, 2-(5-methylthien-2-yl)-5-(thien-2-yl)thiazole, 2,5-bis(5-chlorothien-2-yl)thiazole, 5-(5-methylthien-2-yl)-2-(thien-2-yl)thiazole, 2-(5-chlorothien-2-yl)-5-(5-methylthien-2-yl)thiazole, and 2-(2,2-difluoro-1,3-benzodioxol-5-yl)-5-(5-methylthien-2-yl)thiazole.

The active compounds of this invention can be prepared by elementary modification of synthesis techniques known in the art. Attention is directed, e.g., to U.S. Pat. No. 4,024,156, J. Am. Chem. Soc., 71, 2473 (1949), Synth. Comm., 14, 1 (1984), and U.S. Pat. No. 4,153,703. Preparation of the oxazole/thiazole compounds of this invention is illustrated by the following specific examples. In general, the compounds were characterized by melting point, elemental analysis, and absorption spectra.

EXAMPLE 1

5-(5-Methylthien-2-yl)-2-(4-trifluoromethylphenyl)-thiazole

A warm soluton of 5-methyl-2-acetylthiophene (20.1 g, 0.14 mole) in chloroform (100 ml) was added to a stirred, refluxing mixture of copper (II) bromide (48.0 g, 0.22 mole) in ethyl acetate (100 ml). After complete addition the resultant mixture was heated at reflux for 2.5 hours. The mixture was cooled slightly and filtered. An additional 31.9 g (0.14 mole) of copper(II) bromide was added to the filtrate, and the mixture was heated at reflux for 1.5 hours. The mixture was cooled and filtered. The filtrate was evaporated under reduced pressure yielding 32.1 g of 2-bromo-1-(5-methylthien-2-yl)ethanone as a dark liquid.

A mixture of 2-bromo-1-(5-methylthien-2-yl)ethanone (30.0 g of the aforesaid dark liquid) and hexamethylene tetramine (21.0 g, 0.15 mole) in chloroform (500 ml) was stirred at room temperature for three days. The solvent was removed from the reaction mixture by evaporation under reduced pressure, leaving a dark residue. This residue was stirred in warm methylene chloride. Diethyl ether was added slowly to the mixture, causing a solid to precipitate. After being cooled for several hours, the solid was collected by filtration. The filter cake was rinsed with diethyl ether and was dried under reduced pressure yielding 43.1 g of 1-[2-oxo-2-(5-methylthienyl)ethyl]-3,5,7-triaza-1-azoniatricyclo-[3,3,1,1$^{3,7}$]decane bromide (mp 141° C. dec).

A mixture of 1-[2-oxo-2-(5-methylthienyl)ethyl]-3,5,7-triaza-1-azoniatricyclo[3,3,1,1$^{3,7}$]decane bromide (41.7 g, 0.12 mole) and concentrated hydrochloric acid (50 ml) in ethanol (200 ml) was stirred at room temperature for approximately 18 hours, forming a precipitate. This precipitate was collected by filtration and dried under reduced pressure to yield 26.3 g of a solid. The filtrate was reduced in volume by evaporation to about 100 ml. Diethyl ether was added, causing more precipitate to form. This precipitate was collected by filtration and dried under reduced pressure, yielding 9.0 g of 2-amino-1-(5-methylthienyl)ethanone hydrochloride.

A stirred suspension of 2-amino-1-(5-methylthienyl)ethanone hydrochloride (3.0 g of a mixture containing approximately 60% 2-amino-1-(5-methylthienyl)ethanone hydrochloride) in methylene chloride (100 ml) was cooled in an ice bath. To this cold mixture was added 4-(trifluoromethyl)benzoyl chloride (2.8 g, 0.013 mole), followed by the slow addition of a 2N solution of sodium hydroxide (9.4 ml). After complete addition, the mixture was stirred at room temperature for three days. The mixture was washed first with an aqueous 5% hydrochloric acid solution, followed by water. The organic phase was dried over anhydrous magnesium sulfate and filtered. The filtrate was evaporated under reduced pressure, yielding 3.9 g of N-[2-(5-methylthienyl)-2-oxoethyl]-4-trifluoromethylbenzamide as a solid. A small portion was recrystallized from ethanol for analysis, m.p. 182°–183° C.

To a stirred suspension of Lawesson's Reagent (2.3 g, 0.0057 mole) in approximately 40 ml of toluene was added a mixture of N-[2-(5-methylthienyl)-2-oxoethyl]-4-trifluoromethylbenzamide (3.0 g, 0.011 mole) in toluene (35 ml). After complete addition the reaction mixture was heated at reflux for approximately four hours, then was allowed to cool to room temperature and stirred for two days. The solvent was removed from the reaction mixture by evaporation under reduced pressure, leaving an oil. The oil was dissolved in a small amount of methylene chloride and purified by column chromatography on silica gel, eluting with methylene chloride, yielding 1.0 g of 5-(5-methylthien-2-yl)-2-(4-trifluoromethylphenyl)thiazole as a solid, m.p. 150°–152° C.

EXAMPLE 2

5-(5-Methylthien-2-yl)-2-[3,5-bis(trifluoromethyl)-phenyl]thiazole

In a manner similar to Example 1, the reaction of 2-amino-1-(5-methylthienyl)ethanone hydrochloride (2.6 g, 0.014 mole) in methylene chloride (75 ml) with 3,5-bis(trifluoromethyl)benzoyl chloride (3.8 g, 0.014 mole) and 2N sodium hydroxide solution (13.7 ml) yielded 4.6 g of N-[2-(5-methylthienyl)-2-oxoethyl]-3,5-bis(trifluoromethyl)benzamide as a solid.

In a manner similar to Example 1, the reaction of N-[2-(5-methylthienyl)-2-oxoethyl]-3,5-bis(trifluoromethyl)benzamide (4.0 g, 0.01 mole) in toluene (100 ml) with a suspension of Lawesson's Reagent (2.0 g, 0.005 mole) in toluene (100 ml) yielded 1.0 g of 5-(5-methylthien-2-yl)-2-[3,5-bis(trifluoromethyl)phenyl]thiazole as a solid, m.p. 119.5°–121° C.

EXAMPLE 11

2-(4-Methylphenyl)-5-(thien-2-yl)thiazole

To a stirred mixture of 4-methyl-N-[2-(thien-2-yl)-2-oxoethyl]benzamide (3.01 g, 0.0116 mole) in approximately 20 mL of pyridine was added phosphorous pentasulfide (5.16 g, 0.0116 mole). After complete addition the mixture was heated at reflux for 2.5 hours. The hot mixture was poured into ice water forming a precipitate. This precipitate was collected by filtration. The filter cake was dissolved in methylene chloride and was subjected to column chromatography on silica gel, eluting with methylene chloride, producing a yellow solid. This solid was recrystallized from ethanol to yield 0.96 g of 2-(4-methylphenyl)-5-(thien-2-yl)thiazole, mp 85.5°–86.5° C.

EXAMPLE 31

2-(4-Methylphenyl)-5-(5-methylthienyl-2-yl)thiazole

Under a dry nitrogen atmosphere, a solution of 2-(4-methylphenyl)-5-(thien-2-yl)thiazole (0.17 g, 0.00066 mole) in dry tetrahydrofuran (15 mL) was cooled to −78° C. To this solution was added n-butyl lithium (0.40 mL of a 1.3M solution in hexanes). After complete addition the reaction mixture was stirred at −78° C. for approximately one hour. Methyl iodide (0.1 g, 0.0007 mole) was added, followed by the addition of dimethyl sulfate (0.027 g, 0.00021 mole). The resultant mixture was stirred and allowed to gradually warm to room temperature. To this was added an aqueous saturated ammonium chloride solution. After stirring for a brief period of time the mixture was extracted with methylene chloride. The extract was dried over anhydrous magnesium sulfate and filtered. The filtrate was evaporated under reduced pressure to yield 0.22 g of a yellow solid, mp 108°–110° C. The NMR spectrum indicated the yellow solid was a mixture which contained 85% 2-(4-methylphenyl)-5-(5-methylthien-2-yl)thiazole and 15% 2-(4-methylphenyl)-5-(thien-2-yl)thiazole.

EXAMPLE 40

2-(4-Fluorophenyl)-5-(5-methylsulfonylthien-2-yl)thiazole

To a stirred solution of 2-(4-fluorophenyl)-5-(5-methylthiothien-2-yl)thiazole (1.07 g, 0.0035 mole) in methylene chloride (50 mL) was added dropwise a solution of m-chloroperbenzoic acid (1.7 g, 0.0084 mole) in methylene chloride (25 mL). After complete addition the mixture was stirred at room temperature for approximately 18 hours. Approximately 100 mL of an aqueous 10% sodium sulfate solution was added, and the mixture was stirred for about 15 minutes. The mixture was washed in succession with an aqueous, saturated, sodium bicarbonate solution, water, and an aqueous, saturated, sodium chloride solution. A thin layer chromatograph of the organic phase indicated that starting material remained. Thus the washed organic phase was diluted with methylene chloride, and an additional 1.7 grams of m-chloroperoxybenzoic acid was added. This mixture was stirred and heated at reflux until only one spot was seen by thin layer chromatography. Approximately 100 mL of an aqueous 10% sodium sulfate solution was added, and the mixture was stirred for about 15 minutes. This mixture was washed in succession with an aqueous, saturated sodium bicarbonate solution, water, and an aqueous, saturated, sodium chloride solution. The washed organic phase was evaporated under reduced pressure, leaving a solid residue. This residue was purified by column chromatography on silica gel, elution with methylene chloride-:ethyl acetate (19:1), to yield 0.59 g of 2-(4-fluorophenyl)-5-(5-methylsulfonylthien-2-yl)thiazole as a solid, mp 183°-184° C.

EXAMPLE 50

4-Phenyl-2-(thien-2-yl)thiazole

To a stirred solution of 2-thiophenethiocarboxamide (1.56 g, 0.0109 mole) in ethanol (50 mL) was added 2-bromoacetophenone (2.19 g, 0.0110 mole). After complete addition the mixture was heated at reflux for two hours, then was allowed to cool to room temperature and stir for approximately 18 hours. The solvent was removed from the reaction mixture by evaporation under reduced pressure, leaving an oil which solidified. This solid was suspended in water and extracted twice with methylene chloride. The extracts were combined, dried over anhydrous magnesium sulfate and filtered. The filtrate was evaporated under reduced pressure to yield 2.48 g of 4-phenyl-2-(thien-2-yl)thiazole as a solid, mp 51°-53° C.

EXAMPLE 63

4-(4-Chlorophenyl)-2-(5-chlorothien-2-yl)-5-(4-methylphenyl)thiazole

Under a dry nitrogen atmosphere 2-bromo-2-(4-methylphenyl)-1-(4-chlorophenyl)ethanone (4.5 g, 0.014 mole) and 5-chloro-2-thiophenethiocarboxamide (2.5 g, 0.014 mole) were heated at 110° C. for 2.5 hours. The mixture was cooled and subjected to column chromatography on silica gel, eluting with diethyl ether:n-hexane (5:95), leaving a solid. Recrystallization of this solid from ethanol yielded 0.68 g of 4-(4-chlorophenyl)-2-(5-chlorothienyl-2-yl)-5-(4-methylphenyl)thiazole, mp 103.35°-104.5° C.

EXAMPLE 92

2,5-Di(thien-2-yl)oxazole

A stirred mixture of N-[2-oxoethyl-2-(thien-2-yl)]-2-thiophenecarboxamide (2.02 g, 0.0080 mole) and phosphorus oxychloride (30 mL) was heated at reflux for approximately 18 hours. The mixture was allowed to cool and was poured slowly into ice water. After complete addition the aqueous mixture was stirred to destroy all residual phosphorus oxychloride and then was extracted twice with methylene chloride. The extracts were combined, dried over anydrous magnesium sulfate and filtered. The filtrate was evaporated under reduced pressure, leaving a solid residue. This solid was purified by chromatography, eluting with methylene chloride:n-hexane (50:40), to yield 1.42 g of 2,5-bis(thien-2-yl)oxazole, mp 64.5°-66° C.

Additional azole compounds within the scope of this invention are prepared by similar techniques and are listed in Table 1.

In the normal use of the pesticidal azole compounds of the present invention, the active compounds usually will not be employed free from admixture or dilution, but ordinarily will be used in a suitable formulated composition compatible with the method of application and comprising an insecticidally, acaricidally, or nematicidally effective amount of active compound. The active compounds of this invention, like most pesticidal agents, may be blended with the agriculturally acceptable surface-active agents and carriers normally employed for facilitating the dispersion of active ingredients, recognizing the accepted fact that the formulation and mode of application of a pesticide may affect the activity of the material. The present active compounds may be applied, for example, as sprays, dusts, or granules to the area where pest control is desired, the type of application varying of course with the pest and the environment. Thus, the active compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the active compounds. The granule particles are relatively large, a diameter of about 400-2500 microns typically. The particles are either impregnated with the active compound from solution or coated with the active compound, adhesive sometimes being employed. Granules generally contain 0.05-10%, preferably 0.5-5%, active ingredient as the pesticidally effective amount.

Dusts are admixtures of the active compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide, acaricide, or nematicide. These finely divided solids have an average particle size of less than about 50 microns. A typical dust formulation useful for controlling insects, acarids, or nematodes contains 1 part of active compound, such as 5-(5-methylthien-2-yl)-2-(4-trifluoromethylphenyl)thiazole, and 99 parts of talc.

The active compounds of the present invention may be made into liquid concentrates by dissolution or emulsification in suitable liquids and into solid concentrates by admixture with talc, clays, and other known solid carriers used in the pesticide art. The concentrates are compositions containing, as a pesticidally effective amount, about 5-50% active compound and 95-50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

A typical 50% wettable powder formulation would consist of 50.0% (wt/wt) of 5-(5-methylthien-2-yl)-2-

[3,5-bis(trifluoromethyl)phenyl]thiazole, 22.0% attapulgite diluent, 22.0% kaolin diluent, and 6.0% sodium salts of sulfonated Kraft lignin emulsifier.

Typical carriers for solid concentrates (also called wettable powders) include fuller's earth, clays, silicas, and other highly absorbent, readily wetted inorganic diluents. A solid concentrate formulation useful for controlling insects, acarids, or nematodes contains 1.5 parts each of sodium lignosulfonate and sodium laurylsulfate as wetting agents, 25 parts of 5-(5-methylthien-2-yl)-2-[3,5-bis(trifluoromethyl)phenyl]thiazole, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

A typical 50 gram per liter emulsifiable concentrate formulation would consist of 5.90% (wt/wt) of 5-(5-methylthien-2-yl)-2-(4-trifluoromethylphenyl)thiazole; as emulsifiers: 1.80% of a blend of the calcium salt of dodecylbenzene sulfonate and a nonionic 6-molar ethylene oxide condensation product of nonylphenol, 2.70% of a blend of the calcium salt of dodecylbenzene sulfonate and a nonionic 30-molar ethylene oxide condensation product of nonylphenol, 1.50% of a nonionic paste of polyalkylene glycol ether; and 88.10% refined xylene solvent.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal, acaricidal, or nematicidal composition.

Other useful formulations include simple solutions of the active ingredient in a solvent in which it is completely soluble at the desired concentration, such as acetone or other organic solvents.

An insecticidally, acaricidally, or nematicidally effective amount of active compound in an insecticidal, acaricidal, or nematicidal composition diluted for application is normally in the range of about 0.001% to about 8% by weight. Many variations of spraying and dusting compositions known in the art may be used by substituting the active compounds of this invention into compositions known or apparent in the art.

The insecticidal, acaricidal, or nematicidal compositions of this invention may be formulated with other active ingredients, including other insecticides, nematicides, acaricides, fungicides, plant growth regulators, fertilizers, etc. In using the compositions to control insects, acarids, or nematodes, it is only necessary that an insecticidally, acaricidally, or nematicidally effective amount of azole compound be applied to the locus where control is desired. Such locus may, e.g., be the pests themselves, plants upon which the pests feed, or the pest habitat. When the locus is soil, e.g., soil in which agricultural crops are or will be planted, the active compound may be applied to and optionally incorporated into the soil. For most applications, an insecticidally, acaricidally, or nematicidally effective amount will be about 50 to 750 g per hectare, preferably 150 g to 500 g per hectare.

The pesticidal activity of the active compounds whose preparation is described above was evaluated as follows:

The azole compounds were tested for insecticidal and acaricidal activity under near ultraviolet light (wavelength 320–400 nanometers) at an intensity of 1600–2400 microwatts/cm$^2$ using test procedures adapted to the various organisms in the test. Regardless of the organism, foliage of whole plants or foliage removed from whole plants was sprayed to runoff with a 10% acetone-0.25% octylphenoxypolyethoxyethanol-water solution containing up to 200 ppm of the test compound.

Leaves infested with adult twospotted spider mites (*Tetranychus urticae*) were removed from culture plants and cut into segments containing 50–75 female mites. Each segment was placed on the upper leaf surface of a whole pinto bean (*Phaseolus vulgaris*) plant. After the mites had migrated to the under surfaces of the leaves, the leaf segments used to infest were removed and each plant sprayed with test chemical as described above. After the plants had dried, the entire plant and pot were placed in metal trays in a hood. A supply of water in the tray kept the plants turgid. Tests were conducted against both susceptible and phosphate resistant strains.

In tests utilizing the Mexican bean beetle (*Epilachna varivestis*) or the cabbage looper (*Trichoplusia ni*), the pinto bean test plants were sprayed with test chemical and allowed to dry as previously described. Each test plant was cut off at the soil line and the stem was pushed through a small diameter hole punched in the bottom of an eight ounce waxed container. Ten first instar Mexican bean beetle or cabbage looper larvae were counted into each container. Each container was covered with a glass petri dish and, with the plant stem protruding from the bottom, placed on a holding rack which allowed the stem to remain in water throughout the exposure period.

The test results were collected and recorded at the end of a 24 hour or 48 hour exposure period. These data appear in Table 2. In contrast to the results shown in Table 2, in the absence of ultraviolet irradiation, at application rates of 1000 ppm, the compounds generally failed to kill the insects and acarids.

The azole compounds were evaluated for nematicidal activity against the root-knot nematode (*Meloidogyne incognita*) using aqueous acetone solutions or 5 weight percent dust formulations made up as follows and ground to fine powders:

| | |
|---|---|
| Azole compound (100% active basis) | 5 parts |

-continued

| Base | 95 parts |
|---|---|
| 96%-attapulgite clay | |
| 2%-highly purified sodium lignosulfonate (100%) | |
| 2%-powdered sodium alkylnaphthalenesulfonate (75%) | |

The formulations were tested for activity against root-knot nematode as follows:

Samples of root-knot nematode inoculum were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue", *Proc. Helm. Soc.*, Washington, 22, 87–89 (1955)] and mixed with additional steam-sterilized sandy soil so that there were 600 to 800 root-knot nematode larvae and eggs per pot of soil (three inch diameter each, containing approximately 300 g soil). Depending on the total amount of nematode infested soil needed, mixing was accomplished by use of a cement mixer for 5 minutes or a V-shaped rotary mixer for 60 seconds.

Soil so infested was used for soil-incorporated nematicidal studies within 2 days of preparation. The infested soil was treated with formulations to be tested for nematicidal activity by incorporating the formulation in the soil at 25 ppm or less (weight active compound in mg/soil volume in liters). Young tomato or cucumber plants were planted in this treated, infested soil in three-inch pots. Check plants were planted in the same manner, except untreated, infested soil was used. The formulation base, without active ingredient, was added to infested soil separately and tomato plants grown therein to detect the effects, if any, of chemicals in the formulation base.

At the end of two weeks the roots of all plants were examined and evaluated for galling in comparison to untreated check plants. The results of the tests were expressed in terms of "Percent Control" and appear in Table 3.

Azole compounds of this invention were also tested and found to be effective against southern corn rootworm (*Diabrotica undecimpunctata howardi*) and the free-living nematode *Caenorhabditis elegans*. Activity against the latter is indicative of anthelmintic activity.

TABLE 1

| Ex. | Additional Examples Name | mp (°C.) |
|---|---|---|
| 3 | 2-Phenyl-5-(thien-2-yl)thiazole | 73–74 |
| 4 | 2-(2-Fluorophenyl)-5-(thien-2-yl)-thiazole | 92–93.5 |
| 5 | 2-(2-Trifluoromethylphenyl)-5-(thien-2-yl)thiazole | oil |
| 6 | 2-(3-Fluorophenyl)-5-(thien-2-yl)thiazole | 89–90 |
| 7 | 2-(3-Trifluoromethylphenyl)-5-(thien-2-yl)thiazole | 102–103 |
| 8 | 2-(4-Fluorophenyl)-5-(thien-2-yl)thiazole | 120.5–122 |
| 9 | 2-(4-Chlorophenyl)-5-(thien-2-yl)thiazole | 145.5–147 |
| 10 | 2-(4-Bromophenyl)-5-(thien-2-yl)thiazole | 151–152 |
| 12 | 2-[4-(1,1-Dimethylethyl)phenyl]-5-(thien-2-yl)thiazole | 78.5–80 |
| 13 | 2-(4-Trifluoromethylphenyl)-5-(thien-2-yl)thiazole | 152–153.5 |
| 14 | 2-(4-Cyanophenyl)-5-(thien-2-yl)thiazole | 189.5–191 |
| 15 | 2-(4-Methoxyphenyl)-5-(thien-2-yl)thiazole | 108.5–110 |

TABLE 1-continued

| Ex. | Additional Examples Name | mp (°C.) |
|---|---|---|
| 16 | 2-(4-Pentoxyphenyl)-5-(thien-2-yl)thiazole | 98–99 |
| 17 | 2-[4-(2-Bromo-1,1,2,2-tetrafluoroethoxy)phenyl]-5-(thien-2-yl)thiazole | 90.5–91.5 |
| 18 | 2-(4-Dimethylaminophenyl)-5-(thien-2-yl)thiazole | 136.5–138 |
| 19 | 5-(Thien-2-yl)-2-(4-thiobenzoylphenyl)thiazole | 125.5–127 |
| 20 | 2-[4-(Phenylsulfonyloxy)phenyl]-5-(thien-2-yl)thiazole | 165–166.5 |
| 21 | 2-(2,4-Difluorophenyl)-5-(thien-2-yl)thiazole | 114.5–116 |
| 22 | 2-(3,4-Dichlorophenyl)-5-(thien-2-yl)thiazole | 151.5–153 |
| 23 | 2-[3,5-bis(Trifluoromethyl)phenyl]-5-(thien-2-yl)thiazole | 126.5–127.5 |
| 24 | 2-(4-Fluorophenyl)-5-(3-methylthien-2-yl)thiazole | 56.5–57.5 |
| 25 | 5-(5-Chlorothien-2-yl)-2-(4-fluorophenyl)thiazole | 128.5–129.5 |
| 26 | 2-(4-Bromophenyl)-5-(5-chlorothien-2-yl)thiazole | 162–163.5 |
| 27 | 5-(5-Chlorothien-2-yl)-2-[4-(1,1-dimethylethyl)phenyl]thiazole | 162–163 |
| 28 | 2-(4-Fluorophenyl)-5-(5-methylthien-2-yl)thiazole | 123–124 |
| 29 | 2-(4-Chlorophenyl)-5-(5-methylthien-2-yl)thiazole | 150.5–152 |
| 30 | 2-(4-Bromophenyl)-5-(5-methylthien-2-yl)thiazole | 156–157.5 |
| 32 | 2-(2,4-Difluorophenyl)-5-(5-methylthien-2-yl)thiazole | 100.5–101.5 |
| 33 | 2-(2,4-Dichlorophenyl)-5-(5-methylthien-2-yl)thiazole | 140.5–142 |
| 34 | 2-(3,4-Dichlorophenyl)-5-(5-methylthien-2-yl)thiazole | 170.5–172 |
| 35 | 2-[4-(2-Bromo-1,1,2,2-tetrafluoroethoxy)-3-chlorophenyl]-5-(5-methylthien-2-yl)thiazole | 125.5–127 |
| 36 | 2-(3,5-Dichlorophenyl)-5-(5-methylthien-2-yl)thiazole | 150–152 |
| 37 | 2-(4-Fluorophenyl)-5-[5-(1-hydroxy-2-methylpropyl)thien-2-yl]thiazole | 120–121.5 |
| 38 | 2-(4-Fluorophenyl)-5-[5-(1-hydroxy-2,2-dimethylpropyl)thien-2-yl]thiazole | 152–153 |
| 39 | 2-(4-Fluorophenyl)-5-(5-methylthiothien-2-yl)thiazole | 102–103 |
| 41 | 2-(4-Fluorophenyl)-5-(5-trifluoromethylthiothien-2-yl)thiazole | 86–87 |
| 42 | 2-(4-Fluorophenyl)-5-[5-(3,4,4-trifluoro-3-butenylthio)thien-2-yl]thiazole | 69–70.5 |
| 43 | 2-(4-Fluorophenyl)-5-(5-trimethylsilylthien-2-yl)thiazole | 141–142.5 |
| 44 | 2-(4-Trifluoromethylphenyl)-5-(5-trimethylsilylthien-2-yl)thiazole | 100–101 |
| 45 | 2-(4-Fluorophenyl)-4-trimethylsilyl-5-(5-trimethylsilylthien-2-yl)thiazole | 63–65 |
| 46 | 2-Phenyl-4-(thien-2-yl)thiazole | 70.5–72 |
| 47 | 5-(5-Chlorothien-2-yl)-2-(naphth-1-yl)thiazole | 120.5–121.5 |
| 48 | 5-(5-Chlorothien-2-yl)-2-(naphth-2-yl)thiazole | 163.5–164.5 |
| 49 | 2-Pentafluorophenyl-5-(5-methylthien-2-yl)thiazole | 130.5–132 |
| 51 | 5-Phenyl-2-(thien-2-yl)thiazole | 95–96 |
| 52 | 4-(4-Chlorophenyl)-2-(thien-2-yl)thiazole | 87–88 |
| 53 | 5-(4-Fluorophenyl)-2-(thien-2-yl)thiazole | 138–140 |
| 54 | 5-(4-Chlorophenyl)-2-(thien-2-yl)thiazole | 171–172.5 |
| 55 | 5-Methyl-4-phenyl-2-(thien-2-yl)thiazole | 111–112 |
| 56 | 4,5-Diphenyl-2-(thien-2-yl)thiazole | 121–122 |

TABLE 1-continued
Additional Examples

| Ex. | Name | mp (°C.) |
|---|---|---|
| 57 | 4-(4-Chlorophenyl)-5-phenyl-2-(thien-2-yl)thiazole | 111–112 |
| 58 | 4-(4-Chlorophenyl)-2-(5-chlorothien-2-yl)-5-phenylthiazole | 118–119 |
| 59 | 4-(4-Chlorophenyl)-2-(5-methylthien-2-yl)-5-phenylthiazole | 117–118 |
| 60 | 4,5-bis(4-Chlorophenyl)-2-(thien-2-yl)thiazole | 94–96 |
| 61 | 4,5-bis(4-Chlorophenyl)-2-(5-chlorothien-2-yl)thiazole | 131.5–133 |
| 62 | 4-(4-Chlorophenyl)-5-(4-methylphenyl)-2-(thien-2-yl)thiazole | 154–155 |
| 64 | 4-(4-Chlorophenyl)-5-(4-methylphenyl)-2-(5-methylthien-2-yl)thiazole | 96.5–98 |
| 65 | 2,5-Di(thien-2-yl)thiazole | 91–92 |
| 66 | 2-(5-Chlorothien-2-yl)-5-(thien-2-yl)thiazole | 103.5–105 |
| 67 | 2-(5-Methylthien-2-yl)-5-(thien-2-yl)thiazole | 105.5–107.5 |
| 68 | 2-(5-Chlorothien-2-yl)-5-(3-methylthien-2-yl)thiazole | 86–87 |
| 69 | 2,5-bis(5-Chlorothien-2-yl)thiazole | 122–123.5 |
| 70 | 5-(5-Chlorothien-2-yl)-2-(5-methylthien-2-yl)thiazole | 103.5–104.5 |
| 71 | 5-(5-Methylthien-2-yl)-2-(thien-2-yl)thiazole | 120.5–122 |
| 72 | 2-(5-Chlorothien-2-yl)-5-(5-methylthien-2-yl)thiazole | 114–115.5 |
| 73 | 2,5-bis(5-Methylthien-2-yl)thiazole | 106–107 |
| 74 | 5-(5-Chlorothien-2-yl)-2-([2,2'-bithienyl]-5-yl)thiazole | 187–188 |
| 75 | 2,4-Di(thien-2-yl)thiazole | 49–50.5 |
| 76 | 2-(4-Chlorophenyl)-5-(thien-2-yl)oxazole | 84–85 |
| 77 | 2-(4-Methylphenyl)-5-(thien-2-yl)oxazole | 55–57 |
| 78 | 2-(4-Fluorophenyl)-5-(3-methylthien-2-yl)oxazole | 100–101.5 |
| 79 | 5-(5-Chlorothien-2-yl)-2-(4-fluorophenyl)oxazole | 97–98.5 |
| 80 | 5-(5-Methylthien-2-yl)-2-phenyloxazole | 86.5–87 |
| 81 | 2-(4-Fluorophenyl)-5-(5-methylthien-2-yl)oxazole | 86–87 |
| 82 | 2-(4-Methoxyphenyl)-5-(5-methylthien-2-yl)oxazole | 73.5–75 |
| 83 | 5-Phenyl-2-(thien-2-yl)oxazole | |
| 84 | 5-(4-Fluorophenyl)-2-(thien-2-yl)oxazole | |
| 85 | 5-(4-Chlorophenyl)-2-(thien-2-yl)oxazole | |
| 86 | 5-(4-Methoxyphenyl)-2-(thien-2-yl)oxazole | |
| 87 | 5-([1,1'-Biphenyl]-4-yl)-2-(thien-2-yl)oxazole | |
| 88 | 5-(3-Nitrophenyl)-2-(thien-2-yl)oxazole | 139–142 |
| 89 | 4,5-Diphenyl-2-(thien-2-yl)oxazole | 94–95.5 |
| 90 | 4-(4-Chlorophenyl)-5-phenyl-2-(thien-2-yl)oxazole | 103.5–105 |
| 91 | 4-(4-Chlorophenyl)-5-(4-methylphenyl)-2-(thien-2-yl)oxazole | 116–117.5 |
| 93 | 2-(5-Chlorothien-2-yl)-5-(thien-2-yl)oxazole | 76.77.5 |
| 94 | Ethyl [5-[2-(4-trifluoromethylphenyl)thiazol-5-yl]thien-2-yl]carboxylate | 137–138 |
| 95 | 2-(2,2-Difluoro-1,3-benzodioxol-4-yl)-5-(5-methylthien-2-yl)thiazole | 120–122 |
| 96 | 2-(2,2-Difluoro-1,3-benzodioxol-5-yl)-5-(5-methylthien-2-yl)thiazole | 165–169 |
| 97 | 5-(4-Trifluoromethylphenyl)-2-(5-methylthien-2-yl)thiazole | 148–150 |

TABLE 2
Foliar Testing

| Cmpd. of Ex. | Rate (ppm) | Exposure Time (Hr.) | CL | MBB | TSM-R | TSM-S |
|---|---|---|---|---|---|---|
| 1 | 100 | 24 | 0 | | 100 | 100 |
| | | 48 | | | | 100 |
| 2 | 50 | 24 | | | 73 | 100 |
| | 50 | 48 | 3 | | | |
| | 200 | 24 | | 20 | | |
| 3 | 50 | 48 | | | | 97 |
| 4 | 50 | 24 | | | 100 | 100 |
| | 200 | 24 | | 60 | | |
| 5 | 50 | 24 | | | 23 | 99 |
| | 200 | 24 | 0 | | | |
| 6 | 50 | 24 | | | 55 | 100 |
| | 200 | 24 | | 80 | | |
| 7 | 50 | 24 | | | | 100 |
| | 200 | 24 | | 75 | | |
| 8 | 100 | 24 | | | 99 | |
| | 50 | 48 | | | | 100 |
| 9 | 50 | 48 | | | | 100 |
| 10 | 50 | 24 | | | | 100 |
| | 200 | 24 | | 0 | | |
| 11 | 100 | 24 | | | 100 | |
| | 50 | 48 | | | | 100 |
| 12 | 50 | 24 | | | | 100 |
| | 200 | 24 | | 85 | | |
| 13 | 100 | 24 | | | 100 | |
| | 50 | 48 | | | | 100 |
| 14 | 50 | 24 | | | | 2 |
| | 200 | 24 | | 5 | | |
| 15 | 50 | 24 | | | 100 | 99 |
| | 200 | 24 | 5 | | | |
| 16 | 50 | 24 | | | 94 | 100 |
| | 200 | 24 | | 0 | | |
| 17 | 50 | 24 | | | 100 | 100 |
| | 200 | 24 | | 75 | | |
| 18 | 50 | 24 | | | | 100 |
| | 200 | 24 | | 0 | | |
| 19 | 100 | 24 | | | | 3 |
| | | 48 | | | | 29 |
| | 200 | 24 | | 0 | | |
| | | 48 | | 0 | | |
| 20 | 50 | 24 | | | | 14 |
| | 200 | 24 | | 0 | | |
| 21 | 100 | 24 | | | | 100 |
| 22 | 100 | 24 | | | | 5 |
| | | 48 | | | | 100 |
| 23 | 100 | 24 | | | | 100 |
| 24 | 100 | 24 | | | 93 | |
| | 50 | 48 | | | | 100 |
| 25 | 50 | 48 | | | 100 | 100 |
| 26 | 50 | 24 | | | | 90 |
| | 200 | 24 | | 0 | | |
| 27 | 100 | 24 | | | | 92 |
| 28 | 100 | 24 | | | 100 | 94 |
| | 200 | 24 | 0 | | | |
| 29 | 100 | 24 | | | 97 | 100 |
| 30 | 50 | 24 | | | | 100 |
| | 200 | 24 | | 15 | | |
| 31 | 50 | 24 | | | 97 | 100 |
| | 200 | 24 | 15 | | | |
| 32 | 100 | 24 | | | | 100 |
| 33 | 100 | 24 | | | | 95 |
| 34 | 100 | 24 | | | 80 | 96 |
| | 200 | 24 | | 5 | | |
| 35 | 100 | 24 | | | | 93 |
| 36 | 100 | 24 | | | | 6 |
| | | 48 | | | | 87 |
| 37 | 50 | 24 | | | | 19 |
| | 200 | 24 | | 10 | | |
| 38 | 50 | 24 | | | | 46 |
| | 200 | 24 | | 0 | | |
| 39 | 50 | 24 | | | 89 | 100 |
| | 200 | 24 | | 0 | | |
| 40 | 50 | 24 | | | | 14 |
| | 200 | 24 | | 0 | | |
| 41 | 100 | 24 | | | | 100 |
| | 200 | 24 | | 30 | | |
| 42 | 100 | 24 | | | 97 | 98 |
| | 200 | 24 | | 35 | | |
| 43 | 50 | 24 | | | 99 | 100 |

TABLE 2-continued

Foliar Testing

| Cmpd. of Ex. | Rate (ppm) | Exposure Time (Hr.) | CL | MBB | TSM-R | TSM-S |
|---|---|---|---|---|---|---|
|  | 200 | 24 |  | 10 |  |  |
| 44 | 100 | 24 |  |  | 97 | 100 |
|  | 200 | 24 |  | 0 |  |  |
| 45 | 50 | 24 |  |  |  | 99 |
|  | 200 | 24 |  | 0 |  |  |
| 46 | 50 | 48 |  |  |  | 85 |
| 47 | 50 | 24 |  |  |  | 97 |
|  | 200 | 24 |  | 0 |  |  |
| 48 | 50 | 24 |  |  |  | 99 |
|  | 200 | 24 |  | 0 |  |  |
| 49 | 50 | 24 |  |  |  | 100 |
|  | 200 | 24 |  | 0 |  |  |
| 50 | 100 | 48 |  |  |  | 100 |
| 52 | 50 | 48 |  |  |  | 100 |
| 53 | 50 | 48 |  |  |  | 100 |
| 54 | 50 | 48 |  |  |  | 100 |
| 55 | 50 | 48 |  |  |  | 99 |
| 56 | 50 | 48 |  |  |  | 32 |
| 57 | 50 | 48 |  |  | 3 | 100 |
| 58 | 50 | 24 |  |  |  | 98 |
|  | 100 | 24 |  | 0 |  |  |
| 59 | 50 | 24 |  |  | 100 | 100 |
|  | 200 | 24 | 5 |  |  |  |
| 60 | 50 | 24 |  |  |  | 100 |
|  | 100 | 24 |  | 0 |  |  |
| 61 | 50 | 24 |  |  |  | 35 |
|  | 100 | 24 |  | 80 |  |  |
| 62 | 50 | 48 |  |  | 17 | 96 |
|  | 200 | 48 | 10 | 10 |  |  |
| 63 | 50 | 24 |  |  | 2 | 92 |
|  | 100 | 24 |  | 0 |  |  |
| 64 | 50 | 24 |  |  |  | 77 |
|  | 200 | 24 | 0 |  |  |  |
| 65 | 50 | 48 |  |  | 10 | 100 |
|  | 200 | 48 |  | 0 |  |  |
| 66 | 50 | 48 |  |  | 100 | 100 |
| 67 | 100 | 24 |  |  | 93 |  |
|  | 50 | 48 |  |  |  | 100 |
| 68 | 50 | 24 |  |  | 100 | 100 |
|  | 200 | 24 | 0 |  |  |  |
| 69 | 50 | 24 |  |  | 100 | 100 |
|  | 200 | 24 | 0 |  |  |  |
| 70 | 50 | 24 |  |  | 100 | 100 |
|  | 200 | 24 | 0 |  |  |  |
| 71 | 50 | 24 |  |  | 100 | 100 |
|  | 200 | 24 | 0 |  |  |  |
| 72 | 50 | 24 |  |  | 100 | 99 |
|  | 200 | 24 | 0 |  |  |  |
| 73 | 50 | 24 |  |  |  | 100 |
|  | 100 | 24 |  | 15 |  |  |
| 74 | 50 | 24 |  |  |  | 84 |
|  | 200 | 24 |  | 0 |  |  |
| 75 | 50 | 48 |  |  |  | 98 |
| 76 | 50 | 48 |  |  |  | 71 |
| 77 | 50 | 48 |  |  |  | 92 |
| 78 | 50 | 48 |  |  |  | 100 |
| 79 | 50 | 48 |  |  |  | 100 |
| 80 | 50 | 24 |  |  |  | 87 |
|  | 200 | 24 | 15 |  |  |  |
| 81 | 50 | 24 |  |  |  | 100 |
|  | 200 | 24 | 10 |  |  |  |
| 82 | 50 | 24 |  |  |  | 18 |
|  | 200 | 24 | 15 |  |  |  |
| 83 | 150 | 48 |  |  |  | 100 |
| 84 | 100 | 48 |  |  |  | 0 |
| 85 | 100 | 48 |  |  |  | 31 |
| 86 | 100 | 48 |  |  |  | 0 |
| 87 | 100 | 48 |  |  |  | 0 |
| 89 | 50 | 48 |  |  |  | 100 |
| 90 | 50 | 48 |  |  |  | 10 |
| 91 | 50 | 48 |  |  |  | 86 |
| 92 | 50 | 48 |  |  | 14 | 98 |
| 93 | 50 | 24 |  |  |  | 59 |
|  | 200 | 24 | 0 |  |  |  |
| 94 | 50 | 48 | 70 |  |  | 100 |
| 95 | 50 | 48 | 0 |  |  | 83 |
| 96 | 50 | 48 | 10 |  |  | 100 |

CL = Cabbage looper
MBB = Mexican bean beetle
TSM-R = Twospotted spider mite - resistant
TSM-S = Twospotted spider mite - susceptible

TABLE 3

Evaluation Against Root-Knot Nematode

| Compound of Ex. | Rate of Application (ppm) | Percent Control |
|---|---|---|
| 3 | 10 | 99 |
|  |  | 98 |
| 8 | 10 | 100 |
|  |  | 85 |
| 9 | 10 | 63 |
|  |  | 25 |
| 11 | 10 | 100 |
|  |  | 95 |
|  |  | 33 |
| 24 | 10 | 38 |
|  |  | 75 |
|  |  | 75 |
| 46 | 10 | 98 |
|  |  | 63 |
| 57 | 10 | 0 |
| 64 | 10 | 100 |
|  |  | 0 |
| 66 | 10 | 81 |
|  |  | 8 |
| 71 | 10 | 100 |
|  |  | 25 |
| 75 | 10 | 98 |
|  |  | 95 |
| 77 | 10 | 95 |
|  |  | 42 |
| 79 | 10 | 99 |
|  |  | 68 |
| 85 | 10 | 81 |
|  |  | 96 |

What is claimed is:

1. A compound of the formula

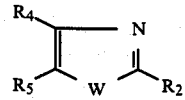

wherein
W is selected from O and S;
$R_2$ is selected from the group consisting of phenyl, naphthyl, 2,2-difluoro-1,3-benzodioxyl, phenyl substituted with at least one substituent selected from halogen, lower alkyl, lower haloalkyl, cyano, lower alkoxy, lower haloalkoxy, di(lower)alkylamino, phenylthiocarbonyl, or phenylsulfonyloxy, thienyl, and thienyl substituted with a substituent selected from halogen, lower alkyl, or thienyl;
$R_4$ is selected from the group consisting of hydrogen, tri(lower)alkylsilyl, phenyl, halophenyl and thienyl;
$R_5$ is selected from the group consisting of hydrogen, phenyl, phenyl substituted with at least one substituent selected from halogen, lower alkyl, lower haloalkyl, lower alkoxy, phenyl, or nitro, thienyl, and thienyl substituted with a substituent selected from lower alkyl, halogen, lower hydroxyalkyl, methylthio, lower haloalkylthio, lower alkylsulfonyl, lower haloalkenylthio, lower alkoxycarbonyl, and tri(lower)alkylsilyl;

wherein at least one of $R_2$ and $R_5$ is an optionally substituted thienyl group and at least one of $R_4$ and $R_5$ is other than hydrogen, with the proviso:

when $R_4$ is hydrogen, phenyl, or thienyl, then $R_5$ is other than hydrogen, phenyl, thienyl, alkylphenyl, or alkylthienyl; or $R_2$ is other than phenyl, alkylphenyl, thienyl or alkylthienyl.

2. The compound of claim 1 selected from the group consisting of 5-(5-methylthien-2-yl)-2-(4-trifluoromethylphenyl)thiazole; 5-(5-methylthien-2-yl)-2-((3,5-bis(trifluoromethyl)phenyl))thiazole; 2-(4-fluorophenyl)-5-(thien-2-yl)thiazole; 2-(4-trifluoromethylphenyl)-5-(thien-2-yl)thiazole; 2-(4-chlorophenyl)-5-(thien-2-yl)thiazole; 2-(4-trifluoromethylphenyl)-5-(thien-2-yl)thiazole; 5-(5-chlorothien-2-yl)-2-(4-fluorophenyl)thiazole; 2,5-bis(5-chlorothien-2-yl)thiazole; 2-(5-chlorothien-2-yl)-5-(5-methylthien-2-yl)thiazole; and 2-(2,2-difluoro-1,3-benzodioxol-5-yl)-5-(5-methylthien-2-yl)thiazole.

3. A compound of claim 1 wherein $R_4$ is hydrogen.

4. A compound of claim 3 wherein $R_5$ is substituted thienyl.

5. The compound of claim 4, 5-(5-methylthien-2-yl)-2-(4-trifluoromethylphenyl)thiazole.

6. The compound of claim 4, 5-(5-methylthien-2-yl)-2-[3,5-bis(tribromomethyl)phenyl]thiazole.

7. An insecticidal, acaricidal, or nematicidal composition comprising in admixture with an agriculturally acceptable carrier an insecticidally, acaricidally, or nematicidally effective amount of at least one compound of the formula

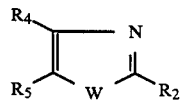

wherein
W is selected from O and S;
$R_2$ is selected from the group consisting of phenyl, naphthyl, 2,2-difluoro-1,3-benzodioxyl, phenyl substituted with at least one substituent selected from halogen, lower alkyl, lower haloalkyl, cyano, lower alkoxy, lower haloalkoxy, di(lower)alkylamino, phenylthiocarbonyl, or phenylsulfonyloxy, thienyl, and thienyl substituted with a substituent selected from halogen, lower alkyl, or thienyl;
$R_4$ is selected from the group consisting of hydrogen, tri(lower)alkylsilyl, phenyl, halophenyl and thienyl;
$R_5$ is selected from the group consisting of hydrogen, lower alkyl, phenyl, phenyl substituted with at least one substituent selected from halogen, lower alkyl, lower haloalkyl, lower alkoxy, phenyl, or nitro, thienyl, and thienyl substituted with a substituent selected from lower alkyl, halogen, lower hydroxyalkyl, methylthio, lower haloalkylthio, lower alkylsulfonyl, lower haloalkenylthio, lower alkoxycarbonyl, and tri(lower)alkylsilyl;
wherein at least one of $R_2$ and $R_5$ is an optionally substituted thienyl group and at least one of $R_4$ and $R_5$ is other than hydrogen, with the proviso:

when $R_4$ is hydrogen, phenyl or thienyl, then $R_5$ is other than hydrogen, phenyl, thienyl, alkylphenyl, or alkylthienyl; or $R_2$ is other than phenyl, alkylphenyl, thienyl or alkylthienyl.

8. The composition of claim 7 selected from the group consisting of 5-(5-methylthien-2-yl)-2-(4-trifluoromethylphenyl)thiazole; 5-(5-methylthien-2-yl)-2-((3,5-bis(trifluoromethyl)phenyl))thiazole; 2-(4-fluorophenyl)-5-(thien-2-yl)thiazole; 2-(4-chlorophenyl)-5-(thien-2-yl)thiazole; 2-(4-trifluoromethylphenyl)-5-(thien-2-yl)thiazole; 5-(5-chlorothien-2-yl)-2-(4-fluorophenyl)thiazole; 2,5-bis(5-chlorothien-2-yl)-thiazole; 2-(5-chlorothien-2-yl)-5-(5-methylthien-2-yl)thiazole, and 2-(2,2-difluoro-1,3-benzodioxol-5-yl)-5-(5-methylthien-2-yl)thiazole.

9. A method for controlling insects, acarids, or nematodes which comprises applying to the locus where control is desired an insecticidally, acaricidally, or nematicidally effective amount of at least one compound of the formula

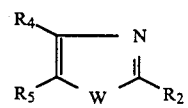

wherein
W is selected from O and S;
$R_2$ is selected from the group consisting of phenyl, naphthyl, 2,2-difluoro-1,3-benzodioxyl, phenyl substituted with at least one substituent selected from halogen, lower alkyl, lower haloalkyl, cyano, lower alkoxy, lower haloalkoxy, di(lower)alkylamino, phenylthiocarbonyl, or phenylsulfonyloxy, thienyl, and thienyl substituted with a substituent selected from halogen, lower alkyl, or thienyl;
$R_4$ is selected from the group consisting of hydrogen, tri(lower)alkylsilyl, phenyl, halophenyl and thienyl;
$R_5$ is selected from the group consisting of hydrogen, lower alkyl, phenyl, phenyl substituted with at least one substituent selected from halogen, lower alkyl, lower haloalkyl, lower alkoxy, phenyl, or nitro, thienyl, and thienyl substituted with a substituent selected from lower alkyl, halogen, lower hydroxyalkyl, lower haloalkylthio, lower alkylsulfonyl, lower haloalkenylthio, lower alkoxycarbonyl, or tri(lower)alkylsilyl;
wherein at least one of $R_2$ and $R_5$ is an optionally substituted thienyl group, and $R_4$ is other than hydrogen when one of $R_2$ and $R_5$ is unsubstituted thienyl and the other of $R_2$ and $R_5$ is unsubstituted phenyl.

10. The method of claim 9 wherein said compound is selected from the group consisting of 5-(5-methylthien-2-yl)-2-(4-trifluoromethylphenyl)thiazole; 5-(5-methylthien-2-yl)-2-[3,5-bis(trifluoromethyl)phenyl]thiazole; 2-(4-fluorophenyl)-5-(thien-2-yl)thiazole; 2-(4-chlorophenyl)-5-(thien-2-yl)thiazole; 2-(4-trifluoromethylphenyl)-5-(thien-2-yl)thiazole; 5-(5-chlorothien-2-yl)-2-(4-fluorophenyl)thiazole; 2-(4-methylphenyl)-5-(5-methylthien-2-yl)thiazole; 2-(5-methylthien-2-yl)-5-(thien-2-yl)thiazole; 2,5-bis-(5-chlorothien-2-yl)thiazole; 5-(5-methylthien-2-yl)-2-(thien-2-yl)thiazole; 2-(5-chlorothien-2-yl)-5-(5-methylthien-2-yl)thiazole; and 2-(2,2-difluoro-1,3-benzodioxol-5-yl)-5-(5-methylthien-2-yl)thiazole.

* * * * *